United States Patent [19]

Segura et al.

[11] Patent Number: 4,759,848
[45] Date of Patent: Jul. 26, 1988

[54] STERILIZATION OF CRYOGENIC LIQUIDS BY ULTRAFILTRATION

[75] Inventors: John S. Segura, West Chester; David E. Connor, III, Douglassville, both of Pa.; Howard D. Brodbeck, New Milford, Conn.

[73] Assignee: MG Industries, Valley Forge, Pa.

[21] Appl. No.: 914,297

[22] Filed: Oct. 2, 1986

Related U.S. Application Data

[63] Continuation-in-part of Ser. No. 694,135, Jan. 23, 1985, abandoned.

[51] Int. Cl.⁴ .............................................. B01D 13/00
[52] U.S. Cl. ..................................... 210/651; 210/184
[58] Field of Search ..................... 210/651, 184, 321.2, 210/DIG. 6, 121, 123, 505, 506, 257.2; 62/317, 318, 319; 55/DIG. 15, 267

[56] References Cited

U.S. PATENT DOCUMENTS 3,238,056  1/1966  Pall et al. ........................ 210/506 X
3,785,490  1/1974  Ryan et al. ....................... 210/123 X Primary Examiner—Frank Spear
Attorney, Agent, or Firm—William H. Eilberg

[57] ABSTRACT

A cryogenic liquid is sterilized by passing it through a microporous filter, while subcooling the liquid. Subcooling virtually eliminates the possiblity of formation of gas bubbles in the liquid, and thereby insures that the desired mass flow of liquid, through the filter, will be maintained. The apparatus used with this invention comprises an insulated tank, filled with cryogenic liquid. A container having a microporous filter disposed therein, is submerged within the tank. The filter can be made of nylon mesh, which is encased within a polypropylene frame. The filter has a pore size of about 0.2 microns or less. The liquid to be sterilized is a saturated cryogenic liquid. The liquid in the tank is held at a temperature lower than that of the liquid to be sterilized, and therefore subcools the liquid being sterilized. The sterilized liquid is then withdrawn directly from the filter container.

16 Claims, 2 Drawing Sheets

STERILIZATION OF CRYOGENIC LIQUIDS BY ULTRAFILTRATION

CROSS REFERENCE TO PRIOR APPLICATION

This is a continuation-in-part of U.S. patent application Ser. No. 694,135, filed Jan. 23, 1985, now abandoned entitled "Sterilization of Cryogenic Liquids by Ultrafiltration".

BACKGROUND OF THE INVENTION

The present invention relates to the field of sterilization of cryogenic liquids. In particular, the invention includes a method and apparatus for sterilizing cryogenic liquids by ultrafiltration means.

Cryogenic liquids are used in many industrial and scientific applications. Often it is required that such liquids be extremely pure. One example of an application requiring a very pure cryogenic liquid is the filling of aluminum cans. Because of the relative softness of aluminum, it is impractical to use that material as a container for foods and beverages because the aluminum cans cannot be stacked. The weight of a stack literally crushes the cans at the bottom of the stack. A solution to this problem is to inject a small amount of a cryogenic liquid into the can, as the can is being filled, immediately before the can is sealed. The cryogenic liquid vaporizes rapidly, creating a substantial pressure within the can, which enables the can to withstand the weight of an entire stack. However, because the cryogenic liquid is mixed with the food or beverage, and is ultimatley ingested by the consumer, such liquid must be absolutely free of bacteria, particulates, and other potentially harmful contaminants. Before a cryogenic liquid may be used for this purpose, there must be assurance that the cryogenic liquid is sterile.

Another example of the need for sterilization of cryogenic liquids is in the medical field. Oxygen used by hospitals is often transported and stored as a cryogenic liquid, since storade space requirements are thereby reduced. The liquid is vaporized when gaseous oxygen is needed. Obviously, it is important that the oxygen administered to a patient be sterile. Still another example of an application requiring purified cryogenic liquids is the process of semiconductor chip fabrication. Such processes are carried out at low temperatures, and require states of extreme cleanliness. The cryogenic liquids used in these processes must therefore be free of all unwanted particles. There are several examples, in the prior art, of the use of filters in gas purification. U.S. Pat. No. 2,924,078 discloses a method of making pure liquid oxygen which includes the use of filters and adsorbers. U.S. Pat. No. 3,739,593 discloses a gas separation system which includes the step of filtering a liquefied gas. U.S. Pat. No. 3,653,220 shows a process for purifying helium, which includes the use of molecular sieves to remove impurities by adsorption. U.S. Pat. No. 3,192,730 discloses a method of purifying liquid helium which includes the step of passing superfluid helium through filters.

The examples of the prior art given above relate generally to chemical purification, and not sterilization. Examples of the use of filters having ultrafine mesh sizes, suitable for sterilization purposes, are shown in U.S. Pat. Nos. 3,974,068 and 4,431,545. U.S. Pat. No. 4,150,548 discloses the use of molecular sieves in the removal of pollutants from gas products.

None of the known prior art references discloses a satisfactory method and apparatus for sterilization of a cryogenic liquid by filter means. The present invention provides such a method and apparatus, which is simple in construction. The invention operates on a pure liquid cryogen, and does not require a phase change. The invention can be used with any cryogenic liquid.

SUMMARY OF THE INVENTION

The present invention comprises a method and apparatus for sterilizing a cryogenic liquid by ultrafiltration. The method comprises the essential steps of passing the liquid through a microporous filter, while subcooling the liquid to prevent gas bubbles from forming. In the preferred embodiment, the mesh size of the filter is about 0.2 microns or less. The sterilized liquid is withdrawn directly from the filter.

The apparatus used to accomplish the above-described steps comprises an insulated tank, into which a filter container is inserted. The tank is filled with a cryogenic liquid, and the filter container is submerged in that liquid. The temperature of the liquid in the tank is maintained at a lower temperature than that of the cryogenic liquid to be sterilized, by keeping the liquid in the tank in liquid form at atmospheric pressure. The level of liquid in the tank is held constant by a float valve assembly, which causes additional liquid to enter the tank, to compensate for the liquid lost due to evaporation. The liquid in the tank may be taken from the same source as the liquid to be sterilized, but the liquid in the tank is not itself sterilized.

Inside the container is a microporous cylindrical filter element. Such a filter element has been made of nylon mesh, having a pore size of about 0.2 microns. This nylon filter can be encased within a frame made of polypropylene. A nylon filter, encased within polypropylene, has been found to operate satisfactorily with subcooled liquid nitrogen, which may have a temperature as low as $-320°$ F.

A conduit delivers cryogenic liquid directly into the container. Because the container is submerged in a liquid which is held at a lower temperature than that of the liquid being sterilized, the liquid being sterilized is subcooled while it is inside the filter container. The subcooling prevents the formation of gas bubbles, and therefore assures that the cryogenic liquid can pass quickly through the ultrafine pores of the filter. Because the liquid being filtered is maintained in a single phase, a relatively large mass flow through the filter can be attained.

It is therefore an object of the present invention to provide a method of sterilizing a cryogenic liquid.

It is another object of the invention to provide a method as described above, wherein small particles and impurities are removed by ultrafiltration.

It is another object of the invention to provide apparatus for sterilizing a cryogenic liquid.

It is another object of the invention to provide apparatus as described above, wherein the liquid to be sterilized can be rapidly passed through the filter element to accomplish the sterilization.

It is an object of the invention to provide a method and apparatus as described above, wherein the method and apparatus are adaptable to any cryogenic liquid.

Other objects and advantages of the invention will be apparent to those skilled in the art, from a reading of the following brief description of the drawings, the detailed description of the invention, and the appended claims.

DETAILED DESCRIPTION OF THE INVENTION

While the present invention will be described with reference to liquid nitrogen, it is understood that the invention can be practiced with any other cryogenic liquid. The only change required, for other liquids, is an adjustment in the temperatures and/or pressures maintained, to suit the particular characteristics of that liquid.

Figure 1:
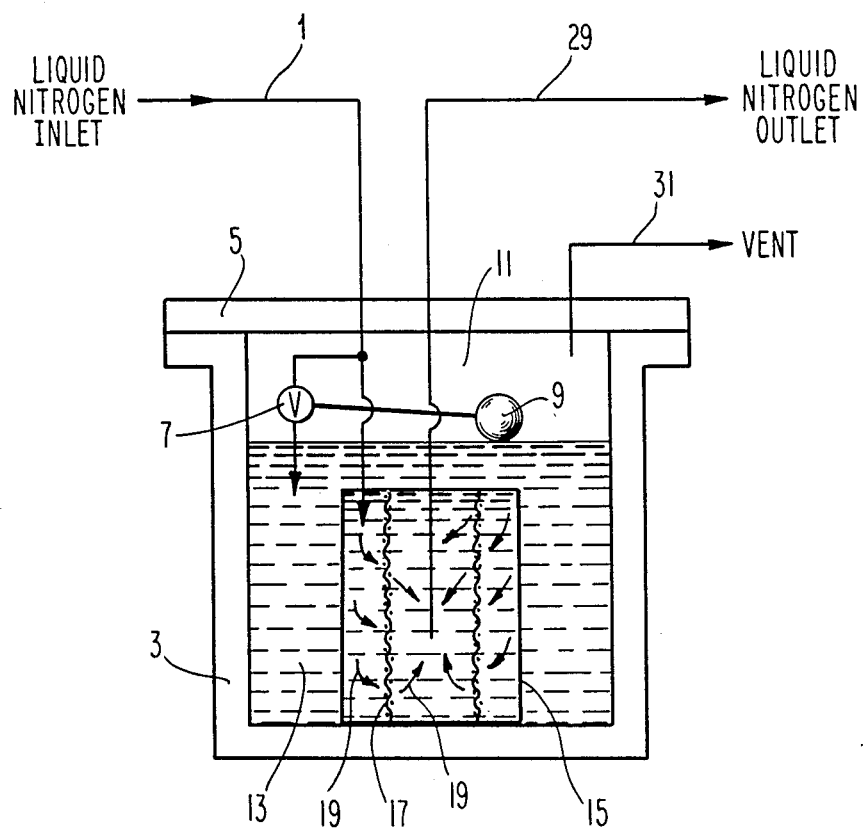
FIG. 1 is a schematic diagram of the apparatus of the present invention.

FIG. 1 illustrates the apparatus of the present invention. Liquid nitrogen is delivered into the apparatus through inlet conduit 1, from an external source. Typically, the incoming liquid nitrogen is maintained, in its external storage means (not shown), at a pressure of 100 psi and at a temperature of −280° F. The apparatus includes insulated tank 3 having lid 5. Tank 3 holds liquid 13, which fills most of the space within the tank. The remainder of the space is occupied by gas head 11.

The level of liquid in tank 3 is maintained by float valve 7 and float ball 9. Liquid nitrogen from conduit 1 is bled off, into valve 7, and into the tank. Float ball 9 senses when the liquid level has fallen below the desired point, and actuates valve 7 to allow more liquid to flow into the tank. The level of liquid in tank 3 is chosen such that filter container 15 is substantially submerged. Except for the requirement that the container 15 be submerged, the level of liquid in the tank is not critical. It should be noted that the liquid which is diverted from conduit 1 through float valve 7 is not sterilized, but is used only to subcool the liquid being sterilized, as explained below.

Filter container 15, which is not thermally insulated, has filter element 17 disposed therein. In the preferred embodiment, the filter element is cylindrical, and is a microporous filter having a mesh size of about 0.2 microns or less.

Liquid nitrogen flowing into the container 15 from conduit 1 travels radially inward, as indicated by arrows 19, and passes through the filter element 17. The filtered liquid is then withdrawn through outlet conduit 29. Conduits 1 and 29 may be provided with seals, at the points where they pass through lid 5. The sealant can be Teflon, nylon, neoprene, or any similar material which can withstand temperatures of the order of −320° F.

A filter apparatus was built, according to the invention, using a filter element formed of nylon mesh, of the type commonly known as "Nylon 66". This material provides a pore size of about 0.2 microns. The nylon was disposed around a cylindrical substrate of polypropylene, and another cylindrical piece of polypropylene surrounded the nylon. The two cylindrical pieces of polypropylene were sealed together, at their ends, by polypropylene caps. The cylindrical pieces of polypropylene thus formed a frame for the nylon filter, holding the filter in place without adhesives, which would block the pores of the filter. The polypropylene itself has a pore size much greater than that of the nylon, and does not play a role in the filtration process.

When the apparatus is in use, conduit 1 is connected to a suitable source of liquid nitrogen, which provides a low-pressure stream of liquid nitrogen, of the order of 3 psi or less. In a test performed with the nylon filter described above, the liquid flowing through the apparatus had a pressure within the range of about 0.7-1.1 psi. Sterilized liquid exiting the apparatus is conveyed to a conventional injector (not shown) and injected into a metal can. Tests performed on the nylon filter have also shown that no significant pressure differential can be observed between the inlet and outlet sides of the apparatus, even after 16 hours of continuous operation. The filter material therefore continues to function satisfactorily, and does not become frozen or clogged.

The filter container 15 is not thermally insulated, so that the liquid within the container can readily transfer heat to the liquid in which the container is submerged. Container 15 is designed to maintain the liquid at its original pressure, which, as mentioned above, may be as high as 100 psi.

The temperature of the liquid 13, in which the filter container is submerged, is held at a temperature lower than that of the incoming liquid. In the preferred embodiment, this temperature is maintained by keeping the nitrogen both in liquid form, and at atmospheric pressure. The nitrogen is kept in liquid form by continuously pouring more liquid nitrogen, from the external source, into the tank. Although some of the nitrogen vaporizes, some liquid always remains. The liquid is maintained at atmospheric pressure due to vent 31. When these two conditions, namely atmospheric pressure and liquid phase, are satisfied, the natural properties of liquid nitrogen dictate that the temperature of the liquid will be −320°. The scientific basis for this phenomenon will be explained below.

The apparatus described, insofar as it provides a means of subcooling a cryogenic liquid, is similar to the structure disclosed in U.S. Pat. No. 4,510,760, entitled "Compact Integrated Gas Phase Separator and Subcooler and Process", and assigned to the same assignee as that of the present application. The disclosure of the cited application is incorporated by reference into the present application. The means of subcooling the liquid in container 15 is essentially the same as that shown in the cited application. It is understood, however, that other means of subcooling the liquid could be employed, within the scope of the present invention.

Although the principal purpose of vent 31 is to maintain the pressure in tank 3 at atmospheric pressure, the vent also serves as a safety device, by preventing dangerous pressure accumulations within the tank.

Figure 2:
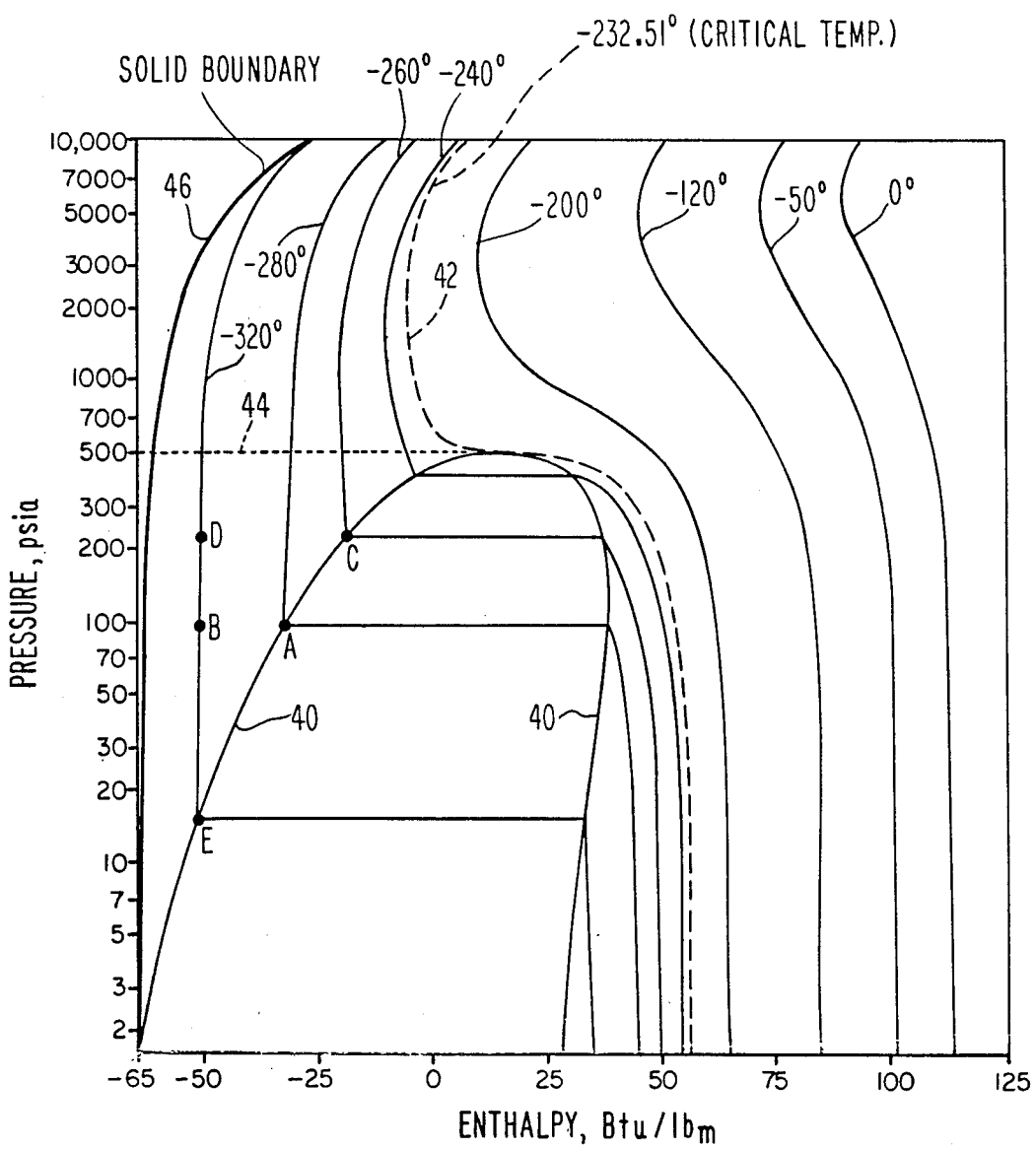
FIG. 2 is a pressure-enthalpy diagram for nitrogen, illustrating the behavior of nitrogen at very low temperatures.

The operation and theory of the invention will be described with reference to FIG. 2, a pressure-enthalpy diagram for nitrogen. FIG. 2 illustrates the behavior of nitrogen at very low temperatures, and for a wide range of pressures. In FIG. 2, dotted line 42 represents the critical temperature for nitrogen, i.e. −232.51° F., above which nitrogen cannot be liquefied. Curved line 40 connects all points at which nitrogen exists as a saturated liquid, i.e. in equilibrium with the gaseous phase. Dotted line 44 represents a pressure of 500 psi; above this pressure, nitrogen cannot be liquefied. Line 46 is labeled "Solid Boundary", and indicates the conditions under which nitrogen becomes a solid.

The region bounded by curve 40, dotted line 44 and solid boundary line 46 is a region in which nitrogen exists as a liquid. The region bounded by the curve 40 and the bottom of the graph is the region in which liquid and gas can both exist. The region to the right of the right-hand portion of curve 40, and to the right of the upper portion of dotted line 42, represents the region in which nitrogen exists only as a gas.

As stated above, liquid 13 is maintained at −320° F. by keeping the bath in liquid form and at atmospheric pressure. The following argument shows why the liquid, under these conditions, must necessarily be at −320° F. First, the state of the liquid must be described by a point on line 40, because the liquid is on the verge of vaporization, and therefore exists in equilibrium with the gas phase. Secondly, vent 31 assures that the pressure of the liquid must be 14.7 psi. The state of this liquid must therefore be represented by point E on FIG. 2 (or along the horizontal line joining the two sides of curve 40). But point E (or any point along the abovedescribed horizontal line) lies on the line along which nitrogen assumes the temperature of −320° F. Thus, the temperature is maintained at this level due to the physics of liquid nitrogen.

In order to maintain the liquid at −320° F., it is therefore necessary that the nitrogen in the tank be maintained as a liquid. This requirement is satisfied by continuously supplying liquid nitrogen to replace the liquid which has vaporized. In this manner, one "pays" for maintaining the nitrogen at the lower temperature.

In the present invention, liquid nitrogen is preferably stored externally at a pressure of 100 psi, and at a temperature of −280° F. Thus, the liquid nitrogen is stored under conditions represented by point A on the graph. Point A lies on curve 40; the liquid nitrogen is thus saturated, and exists in equilibrium with the gas phase.

When the liquid is delivered into filter container 15, it is cooled by the liquid 13 in the tank, the liquid being held at −320° F., as described above. Thus, when so cooled, the liquid nitrogen is moved to point B on the graph. Point B lies in the region wherein the nitrogen is a pure liquid.

Because the liquid being sterilized is maintained at point B, where nitrogen can exist only as a liquid, it is unlikely that gas bubbles will form in the liquid, even if there is some heat leakage. By contrast, if the liquid were still at point A, then any small amount of heat leaking into the container would immediately cause gas bubbles to form. Such bubbles would ruin the effectiveness of the filter. Since a cryogenic liquid, when vaporized, can expand to hundreds of times its previous volume, the formation of gas bubbles would severely clog the filter, and prevent the nitrogen from proceeding through the filter at commercially useful and varying rates. Such bubbles would also create a harmful pressure drop across the filter.

When the liquid passing through the filter is at point B on the graph, a small amount of heat, while tending to move the position of the liquid to the right on the graph, will not cause the liquid to reach point A, In other words, when operating at point B, the liquid will remain a liquid, unless the amount of heat added is sufficient to cause the operating point to reach point A. For this reason, the distance between points A and B represents a margin for error in maintaining the liquid in its single phase condition.

The margin for error discussed above may be made greater or less, depending on the choice of operating pressure and temperature. As seen from the graph, the margin for error depends on the choice of temperatures and pressures used. For example, suppose that the nitrogen is initially stored at −260° F. and at a pressure of about 225 psi (point C on FIG. 2), and that the liquid is then subcooled to −320° F., its pressure being maintained at the same value. Then the nitrogen has been moved to point D, and the margin for error is greater, because the distance between points C and D is greater than the distance between points A and B. On the other hand, the margin for error in the above example would be less if the liquid were not subcooled all the way to −320°.

While the margin for error, discussed above, may be increased, it quickly becomes uneconomical to do so, because of the expense of maintaining the liquid at an elevated pressure. Points A and B represent a good compromise, in the case of nitrogen, and constitute the preferred operating points for that liquid.

As stated above, the present invention can be used with any cryogenic liquid. Each substance has a unique pressure-enthalphy diagram, and it is necessary to consult the particular diagram for the desired cryogenic liquid, in order to determine the optimum pressures and temperatures to be used. For example, another substance can be subcooled, in a manner identical to that described above, i.e. by maintaining the substance as a liquid at atmospheric pressure, but the resulting temperature will be whatever is dictated by the diagram for that liquid.

It is apparent that the objects of the invention are fulfilled by the above disclosure. It is understood that the invention can be modified in various ways. Other means of subcooling the liquid in the container may be used. Also, the means of maintaining the liquid level in the tank may be changed. As explained above, the invention can be practiced with any cryogenic liquid, as long as the proper operating pressures and temperatures are selected. Also, the invention is not limited by the particular choice of materials for the filter and its frame. Materials other than nylon, having the required pore sizes, and being able of withstanding cryogenic temperatures, can also be used as filter elements. The filter frame could also be formed of materials other than polypropylene. These and other modifications are to be deemed within the spirit and scope of the following claims.

What is claimed is:

1. Apparatus for sterilizing a cryogenic liquid, comprising:
   (a) an insulated tank, the tank having a lid, the tank being adapted to store cryogenic liquids, the tank being at least partially filled with a cryogenic liquid,
   (b) a microporous filter, constructed of nylon, the filter having a mesh size of about 0.2 microns, the filter being encased within a frame of polypropylene, the encased filter being disposed within a filter container, the filter container being submerged within the liquid in the tank,
   (c) an inlet conduit connected to an external source of cryogenic liquid, the inlet conduit leading directly into the filter container and terminating on one side of the filter,
   (d) an outlet conduit, one end of which is disposed on the other side of the filter, and
   (e) float valve means for maintaining the level of liquid in the tank at a desired depth.

2. A method of sterilizing a cryogenic liquid, comprising the steps of:
   (a) passing the liquid through a filter having a mesh size of about 0.2 microns or less,
   (b) subcooling the liquid while the liquid is being passed through the filter, and (c) withdrawing the filtered liquid.

3. A method of sterilizing a cryogenic liquid, comprising the steps of:
   (a) providing a cryogenic liquid in a saturated state,
   (b) directing the liquid through a microporous filter,
   (c) subcooling the liquid while the liquid is being passed through the filter, and
   (d) withdrawing the filtered liquid.

4. The method of claim 3, wherein the filter comprises a nylon mesh, having a pore size of about 0.2 microns.

5. The method of claim 4, wherein the subcooling step comprises the steps of maintaining a bath of cryogenic liquid at a temperature below that of the liquid to be sterilized, and submerging the liquid to be sterilized in said bath, whereby heat is transferred from the liquid to be sterilized to the surrounding bath.

6. The method of claim 5, wherein the maintaining step includes the step of controlling the level of liquid of said bath.

7. The method of claim 6, wherein the maintaining step further comprises the step of keeping the bath in liquid form and at atmos-pheric pressure.

8. A method of sterilizing a cryogenic liquid comprising the steps of:
   (a) providing a cryogenic liquid at a known pressure and temperature, the pressure and temperature being selected such that the liquid is in a saturated state,
   (b) passing the liquid through a microporous filter, while cooling the liquid below its original temperature, the cooling step being performed while maintaining the pressure of the liquid substantially at its original value, and
   (c) withdrawing the filtered liquid.

9. The method of claim 8, wherein the cryogenic liquid to be sterilized is nitrogen, wherein the nitrogen is initially maintained at a pressure of about 100 psi and a temperature of about $-280°$ F., and wherein the nitrogen is cooled, in the cooling step, to a temperature of about $-320°$ F.

10. Apparatus for sterilizing a cryogenic liquid, comprising:
    (a) tank means for storing a cryogenic liquid,
    (b) filter container means, disposed within the tank means, the filter container means having ultrafiltration means disposed therein
    (c) means for directing cryogenic liquid from an external source into the filter cotainer means and through the ultrafiltration means, and the source into the tank mean, and
    (d) means for withdrawing the filtered cryogenic liquid from the filter container means,
    wherein the ultrafiltration means comprises a nylon mesh filter, and wherein the filter is encased within a polypropylene frame.

11. The apparatus of claim 10, further comprising means for maintaining the level of liquid in the tank means at a preselected depth.

12. The apparatus of claim 11, wherein the filter container means is substantially submerged within the liquid in the tank means.

13. The apparatus of claim 11, wherein the level maintaining means comprises a float valve assembly.

14. The apparatus of claim 13, further comprising vent means for venting gas out of the tank means.

15. Apparatus for sterilzing a cryogenic liquid, comprising:
    (a) an insulated tank, the tank having a lid, the tank being adapted to store cryogenic liquids, the tank being at least partially filled with a cryogenic liquid,
    (b) a microporous filter having a mesh size of about 0.2 microns or less, the filter being disposed within a filter container, the filter container being submerged within the liquid in the tank,
    (c) an inlet conduit connected to an external source of cryogenic liquid, the inlet conduit leading directly into the fitter container and terminating on one side of the filter,
    (d) an outlet conduit, one end of which is disposed on the other side of the filter, and
    (e) means for maintaining the level of liquid in the tank at a desired depth,
    wherein the microporous filter comprises a nylon mesh having a mesh size of about 0.2 microns, and wherein the filter is encased within a frame of polypropylene.

16. The apparatus of claim 15, wherein the level maintaining means comprises a float valve assembly.

* * * * *